US008323392B2

(12) United States Patent
Jones et al.

(10) Patent No.: US 8,323,392 B2
(45) Date of Patent: *Dec. 4, 2012

(54) OIL-IN-OIL DISPERSIONS STABILIZED BY SOLID PARTICLES AND METHODS OF MAKING THE SAME

(75) Inventors: Tamara K. Jones, Rochester, NY (US); Mridula Nair, Penfield, NY (US)

(73) Assignee: Eastman Kodak Company, Rochester, NY (US)

( * ) Notice: Subject to any disclaimer, the term of this patent is extended or adjusted under 35 U.S.C. 154(b) by 1426 days.

This patent is subject to a terminal disclaimer.

(21) Appl. No.: 11/353,210

(22) Filed: Feb. 13, 2006

(65) Prior Publication Data

US 2007/0189999 A1    Aug. 16, 2007

(51) Int. Cl.
*C08L 91/00* (2006.01)

(52) U.S. Cl. ........... 106/31.6; 359/296; 430/32; 430/38; 204/450

(58) Field of Classification Search .................. None
See application file for complete search history.

(56) References Cited

U.S. PATENT DOCUMENTS

| | | | |
|---|---|---|---|
| 2,932,629 A | 4/1960 | Wiley | |
| 6,080,394 A | 6/2000 | Lin et al. | |
| 6,113,931 A * | 9/2000 | Bonda et al. | 424/401 |
| 6,238,657 B1 | 5/2001 | Lin et al. | |
| 6,529,313 B1 * | 3/2003 | Lin et al. | 359/296 |
| 2002/0155080 A1 * | 10/2002 | Glenn et al. | 424/70.5 |
| 2004/0002429 A1 | 1/2004 | Forbus, Jr. | |
| 2004/0234475 A1 * | 11/2004 | Lannibois-Drean et al. | 424/70.12 |
| 2005/0113482 A1 * | 5/2005 | Wong et al. | 523/160 |
| 2006/0263712 A1 * | 11/2006 | Katano et al. | 430/124 |
| 2007/0002428 A1 * | 1/2007 | Liu et al. | 359/296 |
| 2008/0043317 A1 * | 2/2008 | Hsu et al. | 359/296 |
| 2009/0162779 A1 * | 6/2009 | Nair et al. | 430/137.14 |
| 2010/0215961 A1 * | 8/2010 | Aubry et al. | 428/403 |

FOREIGN PATENT DOCUMENTS

| | | | |
|---|---|---|---|
| EP | 0361931 A1 * | 4/1990 | |
| WO | WO 03/000396 | 1/2003 | |
| WO | WO 2004/068234 | * | 8/2004 |
| WO | WO 2004068234 A1 * | 8/2004 | |

OTHER PUBLICATIONS

Cosgrove, Terence editor; Reynolds, Paul author; Colloid Science—Principles, Methods and Applications, Chapter 9: Wetting of Surfaces; 2005; Blackwell Publishing; pertinent pages: title page and Chapter 9, pp. 159-179.*
Jaitely, V. et al. "Formulation of Oil-in-Oil Emulsions: Potential Drug Reservoirs for Slow Release", 2004, Journal of Drug Delivery Science and Technology, vol. 14, No. 2, pp. 113-117.*
Lide, David R.; and Haynes, W. M. (editors); "CRC Handbook of Chemistry and Physics," 2011, 91$^{st}$ ed. (Internet Edition), section on "Permitivity (Dielectric Constants) of Liquids," pp. 6-186 to 6-207.*
Dinsmore, A. D. et al.; "Colloidosomes: Selectively Permeable Capsules Composed of Colloidal Particles," 2002, AAAS, Science (magazine), vol. 298, pp. 1006-1009.*
Kruglyakov, P.; and Nushtayeva. A.; "Emulsions stabilised by solid particles: the role of capillary pressure in the emulsion films," 2004, Elsevier, "Emulsions: Structure, Stability and Interactions," Chapter 16, pp. 641-676.*
Tomlinson, A. et al.; "Interfacial Characterization of Succinimide Surfactants," 1997, American Chemical Society, Langmuir, vol. 13, No. 22, pp. 5881-5893.*
Sinko, Patrick J.; "Martin's Physical Pharmacy and Pharmaceutical Sciences," 5$^{th}$ ed., 2005, Lippincott, Williams & Wilkins; Chapters 16-18, pp. 437-530.*
Merriam-Webster's Collegiate Dictionary, 11$^{th}$ ed., 2004, entries for "dispersion," "emulsion" and "particle," pp. 361, 409 and 903, respectively.*
Pickering, S. U.; "Emulsions," 1907, American Chemical Society, Journal of the American Chemical Society, vol. 9, pp. 2001-2021.*
Binks, Bernard P.; Clint, John H.; Soild wettability from surface energy components: relevence to Pickering emulsions; 2002; American Chemical Society; Langmuir, vol. 18, pp. 1270-1273.*
Lide, David R.; and Haynes, W. M. (editors); "CRC Handbook of Chemistry and Physics," 2011,91 st ed. (Internet Edition), section on "Permitivity (Dielectric Constants) of Liquids," pp. 6-186 to 6-207.*
Nonomura, Yoshimune et al.; "Self-Assembly of Surface-Active Powder at the Interfaces of Selective Liquids," 2002, American Chemical Society; Langmuir, vol. 18, No. 26, pp. 10163-10167.*
Chin, Byung-Doo et al.; "Rheology and microstructures of electrorheological fluids containing both dispersed particles and liquid drops in a continuous phase," 2000, Journal of Rheology, vol. 44, No. 2, pp. 397-412.*
Ha, Jong-Wook et al.; "Rheological response of oil-in-oil emulsions in an electric field," 2000, Journal of Rheology, vol. 44, No. 2, pp. 235-256.*
Reijon, L et al. "Rhological and dielectric characterization of electrorheological fluids composed of both dispersed particles and liquid drops in a dielectric medium," Electrorheological fluids and magnetorheological suspensions: proceedings of the eighth international conference, 2002, pp. 661-667.*
Hao, Tain (editor); "Electrorheological Fluids: The Non-aqueous suspensions," Elsevier, 2005, Chapters 1 & 4, pp. 1-17 and 114-151.*
The Journal of Colloid and Interface Science, vol. 195, pp. 101-113, (1997), Article No. CS975158, "Characteristics of Electrorheological Responses in an Emulsion System" by Xiao-Dong Pan and Gareth H. McKinley.

(Continued)

*Primary Examiner* — David J Blanchard
*Assistant Examiner* — Ivan Greene
(74) *Attorney, Agent, or Firm* — J. Lanny Tucker

(57) ABSTRACT

In a composition comprising an oil-in-oil emulsion containing a first oil phase dispersed as liquid droplets in a continuous second oil phase, which liquid droplets have a number median diameter of about 1 µm to 10 µm, the liquid droplets are substantially covered with a layer of relatively smaller hydrophobically surfaced solid particles as a result of controlling the size and size distribution of the liquid droplets. The first oil phase optionally further comprises colorant and/or polymer. Also disclosed is a method for making such oil-in-oil emulsions.

17 Claims, No Drawings

OTHER PUBLICATIONS

Journal of Drug Deliver Science and Technology, vol. 14 (2), pp. 113-117, (2004), "Formulation of Oil in Oil Emulsions: Potential Drug Reservoirs for Slow Release" by V. Jaitely, T. Sakthivel, G. Magee, A.T. Florence.

R. M. Wiley, "Limited Coalescence of Oil Droplets in Coarse Oil-in-Water Emulsions," Journal of Colloid Science, vol. 9, No. 5, 1954, pp. 427-436.

J. Bibette, "Depleton Interactions and Fractionated Crystalization for Polydisperse Emulsion Purification," Journal of Colloid and Interface Science, vol. 147, No. 2, Dec. 1991, pp. 474-478.

Xiao-Dong Pan, et al., "Characteristics of Electrorheological Responses in an Emulsion System," Journal of Colloid and Interface Science, vol. 195, 1997, pp. 101-113.

* cited by examiner

OIL-IN-OIL DISPERSIONS STABILIZED BY SOLID PARTICLES AND METHODS OF MAKING THE SAME

CROSS-REFERENCE TO RELATED APPLICATIONS

The present application is related to U.S. application Ser. No. 11/352,586, filed on the same date hereof by Nair et al., and entitled, "OIL-IN-OIL EMULSIONS" and to U.S. application Ser. No. 11/352,587, filed on the same date hereof, by Nair et al., and entitled "ELECTRO-OPTICAL MODULATING DISPLAY DEVICES."

FIELD OF THE INVENTION

The invention relates generally to the field of multi-phase liquid systems and a method of preparing the same, and in particular to a method of preparing liquid particles having controlled and predetermined size and size distribution. In particular, the invention generally relates to oil-in-oil compositions comprising a dispersed oil phase stabilized by solid particles.

BACKGROUND OF THE INVENTION

Colloidal dispersions such as emulsions and suspensions are dispersed systems consisting of two or more mutually insoluble or sparingly soluble liquids. One of the liquids is usually present in excess and is termed the continuous or external phase, while the liquid dispersed in the continuous phase is termed the dispersed, discontinuous or internal phase. If the continuous phase consists of water, and the dispersed phase consists of an organic liquid, such as mineral oil, the term oil-in-water (O/W) emulsion or suspension is used. If water is finely dispersed in an organic or non-aqueous liquid, a water-in-oil (W/O) emulsion or suspension is produced. If two organic liquids are emulsified in each other, the term oil-in-oil (O/O) emulsion or suspension is used. The term emulsion generally refers to particles less than 1 micrometer ($\mu$m) in diameter while the term suspension is usually used to describe particles that are greater than 1 $\mu$m in diameter. However, the terms emulsion and suspension are used herein interchangeably to refer to multi-phase systems in which the size of the dispersed phase can range both less than 1 $\mu$m and greater than 1 $\mu$m.

While O/W and W/O emulsions containing a non-polar oil such as silicone are common, O/O emulsions in which both phases are essentially non-polar are relatively rare. However, the Journal of Colloid and Interface Science, Volume 195, Pages 101-113, Article No. CS975158, Jan. 1, 1997, describes certain paraffin oil-in-silicone oil O/O emulsions, as well as certain silicone oil-in-paraffin oil O/O emulsions. Similarly, emulsions of castor oil in silicone oil, as formulations for drug delivery is described in the Journal of Drug Deliver Science and Technology (2004), 14(2), 113-117.

US Patent Pub. No. 20040002429 describes lubricant compositions comprising an emulsion comprising a low viscosity, relatively non-polar, hydrocarbon carrier fluid and a minor amount of an immiscible or semi-miscible polar, hydrocarbon fluid.

PCT Appl. WO2003/000396 A1 describes emulsions comprising silicones, as either the continuous phase or the dispersed phase, and stabilized by graft and block copolymers, which emulsions are useful for cosmetic applications.

U.S. Pat. No. 6,080,394 A discloses a non-aqueous polar solvent-in-oil emulsion composition containing a non-aqueous polar solvent phase dispersed in a silicone oil continuous phase by an emulsifier. U.S. Pat. No. 6,238,657 B1 describes O/O emulsions, stabilized with silicone elastomers, where one of the oil phases is a silicone oil, while the other oil phase is an organic oil such as mineral oil or castor oil. Also described are three-phase aqueous emulsions derived from such emulsions and their use in personal health care applications.

The formation of O/O emulsions in aliphatic hydrocarbons or the like such as dodecane, which have low dielectric constants, is generally not trivial, especially when certain properties are desired for the two phases in such emulsions. In general, in the formation of emulsions, a stable dispersion of droplets or particles results when the attractive potential between two droplets is less than the repulsive potential. As repulsive potential is directly proportional to the dielectric constant of the dispersion medium, stable dispersions cannot be easily achieved in a medium of very low dielectric constant such as aliphatic hydrocarbons.

Another issue with which to contend, in the case of particles dispersed in low density hydrocarbon solvents such as dodecane is settling of the dispersed phase with time as governed by Stoke's Law that defines settling velocities of particles in a fluid by the following equation:

$$V=(2gr^2)(d_1-d_2)/9\mu$$

where V=velocity of settling, g=acceleration due to gravity, r=radius of particle or dispersed phase, $d_1$=density of dispersed phase, $d_2$=density of medium, and $\mu$=viscosity of the continuous phase. The issue of settling or creaming of particles is especially relevant to electro-optical modulating display devices in which particles are dispersed in a liquid system, such as electrophoretic, electrowetting, or electrochromic display devices. It is important that the particles in such systems remain neutrally buoyant, neither settling nor creaming. Since viscosity and density mismatches of solid particles and the continuous phase in such fluids are usually large, techniques such as increasing the viscosity of the continuous phase using polymeric additives have been employed to overcome this effect, although such solutions can cause the electrical mobility of the particles to be compromised. Another issue, in the case of using silicone oils as the dispersed phase, is that the additives that can be solubilized or dispersed effectively in them, for many such applications, can be limited.

Many of the aforementioned patents and other publications disclose O/O particles that have a fairly broad particle size distribution and none of them disclose particles that can be greater than 1 $\mu$m and possess a narrow particle size distribution at the same time.

The use of solid colloidal silica as a suspending agent in stabilizing oil droplets greater than 1 $\mu$m in an aqueous medium (O/W) has been described by Wiley et al in U.S. Pat. No. 2,932,629. The stabilization is promoted with a water-soluble "promoter" that affects the hydrophobic-hydrophilic balance of the solid colloidal silica particles. As stated in this patent, the promoter drives the particles of the solid colloid to the liquid-liquid interface between the oleophilic or hydrophobic monomer droplets and the aqueous medium.

In view of the above, therefore, there is a need for an O/O composition in which both the continuous phase and the dispersed phase have certain desirable properties, or combinations of properties, which cannot be obtained with prior-art O/O emulsions such as those in which silicone oil is one of the phases. Among the properties which may be desired for both or more of the emulsion phases, depending on the application, is a low dielectric constant or non-polarality. In addition, it may be desired that the dispersed phase be capable of readily incorporating, into the dispersed phase, colorants, polymers, or other additives. It may also be desirable that the dispersed phase comprises droplets having a size greater than 1 µm. O/O compositions with new or improved properties would be advantageously useful in a variety of applications known to the skilled artisan for such materials. In addition, O/O compositions with new or improved properties, not heretofore obtained, would offer the opportunity for the development of new applications for such materials.

SUMMARY OF THE INVENTION

The present invention is directed to overcoming one or more of the problems set forth above. Briefly summarized, one aspect of the present invention relates to a composition comprising an oil-in-oil emulsion containing a first oil phase dispersed as liquid droplets in a continuous second oil phase, which droplets have a predetermined or controlled size and size distribution and a number median diameter of from about 1 µm to 10 µm, wherein the first oil phase is substantially immiscible in the second oil phase, wherein the first oil phase comprises one or more first oils and the second oil phase comprises one or more second oils, the first oil phase optionally further comprising colorant and/or polymer, wherein the liquid droplets are substantially covered or coated with a layer of relatively smaller hydrophobically surfaced solid particles.

Another aspect of the invention comprises a method of making such an oil-in-oil emulsion, wherein a first oil composition comprising one or more first oils is dispersed in a second oil composition comprising one or more second oils in the presence of an effective amount of hydrophobically surfaced solid particles, thereby forming a colloidally stable emulsion, wherein the first oil phase optionally comprising colorant and/or polymer and is in the form of droplets having a predetermined or controlled size and size distribution consistent with a number median diameter of about 1 µm to 10 µm.

The present invention provides an advantageous method of making O/O emulsion particles, less dependent on the chemical nature of the colorant or other components such as functional polymers employed to produce the desired properties of the droplet, as well as providing a dispersed phase that is characterized by a predetermined or controlled size and size distribution.

Thus, the invention contemplates the preparation of O/O compositions incorporating various types of colorant that are soluble or dispersible in a dispersed organic phase that is immiscible with a continuous organic phase. The size and size distribution of the resulting dispersed droplets can be predetermined and controlled by the relative quantity and size, relative to the dispersed phase, of the hydrophobically surfaced solid particles, also referred to as a particulate suspension stabilizer. In a preferred embodiment, the hydrophobically surfaced solid particles are silica particles that have been reacted with a silating agent to render hydrophobic the surface of the silica particles. The O/O compositions have excellent stability to coalescence, do not settle due to extremely low settling rates and are neutrally buoyant. The dispersed droplets preferably have a size greater than 1 µm and a narrow particle size distribution. In one preferred embodiment, the two phases of the emulsion, a continuous and a dispersed or discontinuous phase, have matched refractive indices and the dispersed phase is colored differently than the continuous phase. Such O/O compositions are advantageous for providing a substantially common surface for a variety of different colorants due to effective encapsulation of the colorants by the oil in the dispersed oil phase and the surrounding particulate stabilizer, thereby providing more predictable behavior across a given color series, depending on the particular application including imaging systems such as electrically driven displays, liquid toning systems, electrostatic printing inks, and the like.

The term "oil" refers to a liquid compound that is not miscible with water, generally combustible, although preferably non-volatile, and soluble in ether. The term "oil composition" refers to one or more oils, including a mixture of oils or single oil.

The term "dielectric constant" refers to the measure of the ability of the material to support an electric field and is a measure of the polarity of the material. The dielectric constant "∈" of a medium is its ability to reduce the force of attraction F of charged particles $q_1$ and $q_2$ separated at distance r compared to a vacuum. The dielectric constant "∈" is defined here by the equation, $F=q_1 q_2/(\in r)$. Dielectric constants for some familiar substances are as follows: water, 80.4; methanol, 33.6; and benzene, 2.3. High-dielectric constant solvents such as water usually have polar functional groups, and often, high dipole moments.

The term "phase" is meant to refer to the entire composition of the phase, including both the liquid oil composition and any additives dissolved or dispersed therein. The terms "oil composition," "fluid carrier," or "fluid" refer to the total organic solvent, or mixture of liquid organic solvents, included in an oil phase, which solvents are inherently liquid in pure form at room temperature, not including inherently solid materials dissolved or dispersed solids in the liquid. Depending on the context, various properties may refer to either the entire composition of a phase or only the oil composition in the phase.

DETAILED DESCRIPTION OF THE INVENTION

The present invention relates to oil-in-oil (O/O) compositions comprising droplets of a discontinuous oil phase containing a low dielectric, essentially non-volatile organic liquid, such as an organic phosphate liquid or a silicone oil, dispersed in a continuous phase of another low dielectric organic liquid such as an essentially non-volatile hydrocarbon, using a solid particulate stabilizer such as hydrophobically surfaced silica particles. The composition can further include a colorant. The dispersed phase in such emulsions have a number median diameter of at least about 1 µm, have excellent stability to coalescence, and can be controlled to have a relatively very narrow particle size distribution. The emulsions can be formulated by a relatively simple, and inexpensive process.

The fluid carrier for the continuous oil phase can be chosen based upon properties such as dielectric constant, boiling point, and solubility, depending on the application. In one embodiment, a preferred fluid has a low dielectric constant (less than 10), a high boiling point (greater than 100° C. at atmospheric pressure) and viscosity less than 50 cP at 25° C. The discontinuous phase fluid preferably has a solubility in the continuous phase fluid of less than 1 percent by weight at room temperature. Further, to minimize the settling velocity of the dispersed phase in the O/O emulsion and maintain neutral buoyancy of the emulsion droplets, according to Stokes Law, the difference in density between the discontinuous and continuous phases should be small and the number median particle size of the dispersed phase droplets should be sufficiently small.

The choice of oil for the continuous phase may further be based on chemical inertness and chemical compatibility with the dispersed oil phase. The viscosity of the fluid should be low when movement of the dispersed droplets is desired, such as when the emulsion is used in an electro-optical modulated field. For applications in which it is desired to optimize the light transmission through the O/O composition, it may be desired to minimize scattering by substantially matching the refractive index of the continuous phase fluid to that of the droplets. As used herein, the refractive index of the continuous phase or its carrier fluid "is substantially matched" to that of the dispersed phase or its carrier fluid if the difference between their respective refractive indices is between about zero and about 0.3, preferably between about 0.05 and about 0.2. Additionally, the fluid for the continuous phase may be chosen to be a poor solvent for some polymers or colorants which are incorporated into the dispersed oil phase, advantageously for the fabrication of droplets, because such a condition increases the range of materials that can be used in fabricating dispersions of droplets containing polymers and colorants.

Regarding the continuous phase, organic solvents, such as saturated linear or branched hydrocarbons of the general formula $C_nH_{2n+2}$ where n can be between 6-20 or alkanes, aromatic hydrocarbons, halogenated organic solvents, and silicone oils are a few suitable types of liquid fluids for the continuous phase, which fluid may comprise a single fluid. The fluid, however, can also be a blend of more than one oils in order to tune its chemical and physical properties. Useful hydrocarbons include, but are not limited to, octane, decane, dodecane, tetradecane, xylene, toluene, naphthalene, hexane, cyclohexane, benzene, the aliphatic hydrocarbons in the ISOPAR series (Exxon), NORPAR (a series of normal paraffinic liquids from Exxon), SHELL-SOL (Shell), SOL-TROL (Shell), naphtha, and other petroleum solvents such as superior kerosene, paraffin oil, white mineral oil, molex raffinate, or suitable mixtures thereof. These materials usually have low densities. Useful examples of silicone oils include, but are not limited to, octamethyl cyclosiloxane and higher molecular weight cyclic siloxanes, poly(methyl phenyl siloxane), hexamethyldisiloxane, and polydimethylsiloxane. These materials also usually have low densities. Other useful organic solvents include, but are not limited to, epoxides, such as, for example, decane epoxide and dodecane epoxide; and vinyl ethers, such as, for example, cyclohexyl vinyl ether.

Furthermore, the continuous phase fluid may contain surface modifiers to modify the surface energy or charge of the dispersed oil droplets. Preferably, the fluid is clear or transparent and does not itself exhibit any color, although, again, such is not prohibited by the present invention as discussed above. The continuous phase is preferably a low-dielectric composition and substantially free of ions.

Oils for the dispersed or discontinuous phase in the O/O emulsions according to this invention are non-volatile, preferably non-polar liquids, preferably an organic phosphate liquid or a silicone oil in one embodiment. Preferred organic phosphate liquids includes, for example, branched or unbranched alkyl, cycloalkyl, alkylcycloalkyl, aryl, and alkylaryl phosphates-based solvents such as dialkyl, diaryl, trialkyl and triaryl phosphates, in which the organic groups may be substituted or unsubstituted, preferred substituents including non-polar groups such as halogens and ethers. In a preferred embodiment, each alkyl group of the di- or trialkyl phosphate has one to ten carbon atoms, more preferably two to eight carbon atoms. The aryl groups may be ring substituted such as, for example, in tricresyl phosphate. The alkyl or aryl groups of the di- or trialkyl and aryl phosphate can all be the same or can be different. A particularly preferred trialkyl phosphate is triethyl phosphate. Mixtures of different liquid organic phosphates, such as mixtures of dialkyl and trialkyl phosphates or diaryl and triaryl phosphates can be employed. Preferably, these phosphates have a boiling point greater than about 100° C. at atmospheric pressure, a dielectric constant less than 25, and a viscosity less than 100 P at 25° C. and are substantially insoluble in the continuous phase. Further, after incorporation of polymers and optionally colorants in the dispersed oil phase liquids, it is preferred that the final viscosity be less than 200 cP and more preferably less than 100 cP at 25° C. for ease of dispersibility in the continuous phase.

The oil for the dispersed phase must be capable of being formed into small droplets in the continuous phase at the temperature at which the droplets are formed. Processes for forming small droplets include flow-through jets, membranes, nozzles, or orifices, as well as high shear emulsifiers and high-pressure homogenizers. The formation of small droplets may be assisted by the use of electrical or sonic fields.

Solid particle stabilizers having a hydrophobic surface are used to aid in stabilization during or after emulsification of the dispersed phase in the continuous phase. Various inorganic particles, including metallic oxides such as alumina or silicon-containing oxides, surface treated with a hydrophobic material, may be suitably used. Alternately, suitable solid organic colloidal particles, for example, co-polymer particles such as described in U.S. Pat. No. 4,965,131 may be used as the solid particulate stabilizer.

A particularly preferred hydrophobically surfaced solid particle stabilizer is referred to as hydrophobic silica. Such silica particles have an average particle size of from 0.1 nm to 5 mm prior to homogenization with the oils. During homogenization, the silica particles break up and undergo a particle size reduction to less than 500 nanometers (nm), as measured by transmission electron microscopy. It is these particles that effectively surround and stabilize the disperse phase. The reduced hydrophobic silica particles have dimensions from about 10 to 300 nm and preferably from about 30 to 150 nm. The size and concentration of these particles control the size of the dispersed phase droplets. Although hydrophobic silicas are preferred, other hydrophobic or non-polar oil dispersible solid organic and/or inorganic particulates can be used, as mentioned above.

Hydrophobic silica for use in forming the O/O compositions of this invention include various fumed silicas that have been surface treated with reactive silicon-containing compounds such as commercially available silating agents that can impart hydrophobicity to the silica surface. Particularly useful hydrophobic silicas include NANOGEL and CAB-O-SIL TS 610 from Cabot Corporation. Blends of silicas can also be used to achieve the necessary stabilization.

Suitably, the hydrophobically surfaced solid particles are present at a concentration of from 5 to 75 weight percent with respect to the dispersed oil phase, preferably in an amount of from 5 to 50 weight percent of the dispersed oil phase.

The hydrophobically surfaced solid particle stabilizer is preferably used in conjunction with a co-stabilizer that is soluble in the continuous oil phase. More specifically, the co-stabilizer promotes or enhances the adsorption of the hydrophobically surfaced solid particle stabilizer at the interface of the disperse phase oil droplets and the non-polar continuous oil phase. In particular, this combination of co-stabilizer and particle stabilizer, aids in keeping the dispersed phase droplets well dispersed in the continuous phase, thereby prolonging the shelf life of the O/O composition, especially when containing a dispersion of the one non-polar oil in another. Any suitable co-stabilizer that is soluble in the continuous organic phase and favorably affects the surface energetics of the solid particle stabilizer in the continuous phase may be employed in order to drive the solid particle stabilizer to the interface between the dispersed phase liquid droplets and the continuous phase. Such compounds can comprise at least two different segments or moieties, a first segment comprising moieties attracted to the dispersed phase and a second segment comprising continuous-phase soluble moieties. For example, a first segment may comprise amine groups and a second segment may comprise repeat units of an non-polar monomer, for example, isobutylene or the like. Useful co-stabilizers include for example, those compounds commercially sold under the trademarks OLOA (Chevron) and SOLSPERSE (Noveon). SOLSPERSE 13940, for example, is a polyesteramine (aziridine-hydroxy stearic acid copolymer. A preferred co-stabilizer is OLOA 11000 which is a polyethyleneimine substituted succinimide derivative of polyisobutylene.

Still another class of co-stabilizers useful for the practice of the present invention is derived from small organic amine containing molecules, particularly, heterocyclic amines. Some preferred examples are, N-(1-acetyl-2,2,6,6-tetramethyl-4-piperidinyl)-2-dodecylsuccinimide (SANDUVOR 3058); 2-dodecyl-N-(2,2,6,6-tetramethyl-4-piperidinyl)-succinimide (SANDUVOR 3055); and 2-dodecyl-N-(1,2,2,6,6-pentamethyl-4-piperidinyl)-succinimide (SANDUVOR 3056).

Generally, the co-stabilizer is used in an amount of from 1 to 15 percent by weight of the solid particle stabilizer and more preferably from 1-10 percent by weight.

As indicated above, the dispersed phase of the O/O composition can, and preferably does, include useful ingredients, for example, a pigment, a polymer, a laked pigment, a dye, a pigment-polymer composite, a dye-polymer composite or some combination of the above. Preferably the pigment, polymer, and/or pigment-polymer composite is present in the dispersed oil phase in a total amount of from 1 to about 50 percent by weight of the dispersed phase, and oil in the dispersed phase is present in the amount of from 50 to 99 percent by weight of the dispersed phase. In one embodiment, the dispersed oil phase comprises colorant (including pigment or dye) in an amount 1 to 30 percent, preferably 1 to 15 percent, by weight of the dispersed first oil phase and 0.1 to 60 percent, preferably 1 to 40 percent, by weight of one or more polymers molecularly dissolved in the dispersed oil phase. A pigment, laked pigment, or pigment-polymer composite, in order to be dispersed in the dispersed phase, should have an average particle diameter sufficiently small relative to the diameter of the dispersed first oil phase, preferably an average particle diameter on average 10 to 100 nm.

In one embodiment, a pigment-polymer composite may be formed by a physical process such as melt-compounding the polymer and colorant, followed by grinding, attrition, or ball milling. Such composites have been previously used for making conventional xerographic toners and are well known in the art, including the polymers and colorants used to make such toners, and are commercially available from any number of suppliers. A pigment-polymer composite can be mixed into the oil fluid for the dispersed phase by stirring in the composite until the polymer dissolves in the oil. The pigment may also be milled in the oil for the dispersed phase with or without the polymer present. The pigment in the pigment-polymer composite may be present in an amount of from 0.1 to 80 percent by weight of the pigment-polymer composite. The pigment-polymer composite can be used in amounts of from 1 to about 50 percent by weight of the dispersed phase, preferably from 5-30 percent by weight, and most preferably from 10-25 percent by weight.

Polymers useful in the practice of this invention, for incorporation in the oil droplets, with or without a colorant, preferably are oil-soluble resins and include, but are not limited to, homopolymers and copolymers such as polyesters, styrenes, e.g. styrene and chlorostyrene; monoolefins, e.g. ethylene, propylene, butylene and isoprene; vinyl esters, e.g. vinyl acetate, vinyl propionate, vinyl benzoate and vinyl butyrate; a-methylene aliphatic monocarboxylic acid esters, e.g. methyl acrylate, ethyl acrylate, butyl acrylate, dodecyl acrylate, octyl acrylate, phenyl acrylate, methyl methacrylate, ethyl methacrylate, butyl methacrylate and dodecyl methacrylate; vinyl ethers, e.g. vinyl methyl ether, vinyl ethyl ether and vinyl butyl ether; and vinyl ketones, e.g. vinyl methyl ketone, vinyl hexyl ketone and vinyl isopropenyl ketone and mixtures thereof. Particularly desirable binder resins include polystyrene resin, polyester resin, styrene/alkyl acrylate copolymers, styrene/alkyl methacrylate copolymers, styrene/acrylonitrile copolymer, styrene/butadiene copolymer, styrene/maleic anhydride copolymer, polyacrylonitrile resin, polyethylene resin and polypropylene resin and mixtures thereof. They further include polyurethane resin, epoxy resin, silicone resin, polyamide resin, polycaprolactone resin, modified rosin, paraffins and waxes and mixtures thereof. In a preferred embodiment the resins most preferred for the O/O compositions are polyesters and are soluble in the oil for dispersed phase. Suitable polyester resins include polyesters derived from bisphenol A. One preferred polymer is a polyester, for example, TUFTONE NE-303 (Kao Corporation), a polyester copolymer of bisphenol A.

Optional polymers for the dispersed phase may be selected based on the desired properties to be imparted by the inclusion of the polymers, depending on the particular application. For example, a polymer may be used that is designed or preselected to be functionalized with a charged group in order to control mobility of the dispersed phase through the continuous phase when the emulsion composition is subjected to an electric or magnetic field. The polymer may also be selected to affect the viscosity of the dispersed oil-phase droplets.

Dyes useful in this invention can be a pure compound, or blends of dyes to achieve a particular color, including black. The dyes can be fluorescent. photoactive, changing to another color or becoming colorless upon irradiation with either visible or ultraviolet light. Dyes could also be polymerizable by, for example, thermal, photochemical or chemical diffusion processes, forming a solid absorbing polymer inside the droplet. Properties desired for the dyes include light fastness, solubility in the suspending liquid, and color. Low cost is a factor. These dyes are generally chosen from the classes of azo, anthraquinone, and triphenylmethane type dyes and may be chemically modified so as to increase their solubility in the oil phase. Useful azo dyes include, but are not limited to: the Oil Red dyes and the SUDAN Red and SUDAN Black series of dyes. Useful anthraquinone dyes include, but are not limited to: the Oil Blue dyes, and the MACROLEX Blue series of dyes. Useful triphenylmethane dyes include, but are not limited to, Michler's hydrol, Malachite Green, Crystal Violet, and Auramine O.

A neat pigment can be any pigment, and, usually for a light colored particle, pigments such as rutile (titania), anatase (titania), barium sulfate, kaolin, or zinc oxide are useful. Some typical particles have high refractive indices, high scattering coefficients, and low absorption coefficients. Other particles are absorptive, such as carbon black or colored pigments used in paints and inks. The pigment should also be insoluble in the continuous phase. Yellow pigments such as diarylide yellow, HANSA yellow (Clariant), and benzidine yellow have also found use in similar displays. Any other reflective material can be employed for a light colored particle, including non-pigment materials, such as metallic particles.

Useful neat pigments include, but are not limited to, PbCrO4, SUNFAST Blue 15:3, SUNFAST Magenta 122, Cyan blue GT 55-3295 (American Cyanamid Company, Wayne, N.J.), CIBACRON Black BG (Ciba Company, Inc., Newport, Del.), CIBACRON Turquoise Blue G (Ciba), CIBALON Black BGL (Ciba), ORASOL Black BRG (Ciba), ORASOL Black RBL (Ciba), Acetamine Black, CBS (E.I. DuPont de Nemours and Company, Inc., Wilmington, Del., hereinafter abbreviated "DuPont"), CROCEIN Scarlet N Ex (DuPont) (27290), FIBER BLACK VF (DuPont) (30235), LUXOL FAST BLACK L (DuPont) (Solv. Black 17), NIROSINE Base No. 424 (DuPont) (50415 B), OIL BLACK BG (DuPont) (Solv. Black 16), ROTALIN BLACK RM (DuPont), SEVRON BRILLIANT RED 3B (DuPont); Basic Black DSC (Dye Specialties, Inc.), HECTOLENE Black (Dye Specialties, Inc.), AZOSOL Brilliant Blue B (GAF, Dyestuff and Chemical Division, Wayne, N.J.) (Solv. Blue 9), AZOSOL Brilliant Green BA (GAF) (Solv. Green 2), AZOSOL Fast Brilliant Red B (GAF), AZOSOL Fast Orange RA Conc. (GAF) (Solv. Orange 20), AZOSOL Fast Yellow GRA Conc. (GAF) (13900 A), Basic Black KMPA (GAF), BENZOFIX Black CW-CF (GAF) (35435), CELLITAZOL BNFV Ex Soluble CF (GAF) (Disp. Black 9), CELLITON Fast Blue AF Ex Conc (GAF) (Disp. Blue 9), CYPER Black IA (GAF) (Basic Black 3), DIAMINE Black CAP Ex Conc (GAF) (30235), Diamond Black EAN Hi Con. CF (GAF) (15710), Diamond Black PBBA Ex (GAF) (16505); Direct Deep Black EA Ex CF (GAF) (30235), HANSA Yellow G (GAF) (11680); INDANTHRENE Black BBK Powd. (GAF) (59850), INDOCARBON CLGS Conc. CF (GAF) (53295), KATIGEN Deep Black NND Hi Conc. CF (GAF) (15711), RAPIDOGEN Black 3 G (GAF) (Azoic Black 4); SULPHONE Cyanine Black BA-CF (GAF) (26370), ZAMBEZI Black VD Ex Conc. (GAF) (30015); RUBANOX Red CP-1495 (The Sherwin-Williams Company, Cleveland, Ohio) (15630); REGAL 330 (Cabot Corporation), RAVEN 11 (Columbian Carbon Company, Atlanta, Ga.), (carbon black aggregates with a particle size of about 25 µm), STATEX B-12 (Columbian Carbon Co.) (a furnace black of 33 µm average particle size), and chrome green.

Laked pigments are particles that have a dye precipitated on them and are metal salts of readily soluble anionic dyes. These are dyes of azo, triphenylmethane or anthraquinone structure containing one or more sulphonic or carboxylic acid groupings. They are usually precipitated by a calcium, barium or aluminum salt onto a substrate. Typical examples are PEACOCK BLUE lake (C1 Pigment Blue 24) and PERSIAN ORANGE (lake of C1 Acid Orange 7), BLACK M TONER (GAF) (a mixture of carbon black and black dye precipitated on a lake).

The pigment-polymer composite may also contain, in addition to the pigment and polymer, other additives such as organo-cations, for example, quaternary ammonium and phosphonium compounds. Specific examples of these include, but are not limited to, lauramidopropyltrimethylammonium methylsulfate, octadecyldimethylbenzylammonium m-nitrobenzenesulfonate, methyltriphenylphosphonium tetrafluoroborate, and methyltriphenylphosphonium tosylate.

The dispersed oil-phase droplets as described herein can be prepared by forming discontinuous droplets of one or more first oils in a continuous phase of the one or more second oils in the presence of the hydrophobically surfaced solid particle stabilizer and the co-stabilizer, reducing the size of the dispersed oil-phase droplets, and limiting the coalescence of the droplets by the action of the solid particle stabilizer on the surfaces of the droplets. Any type of mixing and shearing equipment may be used to perform these steps such as a batch mixer, planetary mixer, single or multiple screw extruder, dynamic or static mixer, colloid mill, high pressure homogenizer, sonicator, or a combination thereof. While any high shear type agitation device is applicable to the process of this invention, a preferred homogenizing device is the MICROFLUIDIZER such as Model No. 101T produced by Microfluidics Manufacturing. In this device, the droplets of the dispersed oil phase are dispersed and reduced in size in the continuous phase in a high shear agitation zone and, upon exiting this zone, the particle size of the dispersed phase is reduced to uniform sized dispersed oil-phase droplets in the continuous phase. Each of the dispersed oil-phase droplets are surrounded by hydrophobically surfaced solid particle stabilizer, which within predetermined limits, limits and controls both the size and size distribution of the liquid droplets. In one embodiment, the hydrophobically surfaced silica particles are first broken up into smaller size particles in the continuous phase prior to combining with one or more of the first oils.

As indicated, after exiting the homogenizer, the particle size of the liquid droplets can be substantially established. Thus, the dispersed phase droplets remain in the continuous phase surrounded by the hydrophobic silica particles. For example, the process for making the O/O composition can be carried out by combining pigment-polymer composite dispersed in the one or more oils of the dispersed phase with the one or more oils of the continuous phase containing hydrophobic silica or other solid particle stabilizer and the co-stabilizer, such that the dispersed phase is present at a weight percent of 1-50 weight percent, preferably 5-40 weight percent, of the continuous phase, and vigorously mixing the ingredients using any suitable device including high speed agitation, ultrasonic devices, high pressure homogenizers, and the like in order to reduce the particle size of the dispersed phase droplets to less than that ultimately desired. The temperature of the process can be modified to achieve the optimum viscosity for emulsification of the droplets. The presence of the solid particle stabilizer then controls the level of coalescence that takes place until an equilibrium is reached and the particle size does not grow any further. The number median particle size of the dispersed droplets of the O/O composition as described in this invention is preferably from about 1-10 µm and more preferably from about 1-5 µm.

In accordance with this invention, the quantities of the various ingredients and their relationship to each other can vary over wide ranges, depending upon the desired final properties of the O/O composition. The size and quantity of the dispersed oil-phase droplets depends upon the size and quantity of the particles of the solid particle stabilizer. Thus, as the size of the dispersed oil-phase droplets are made smaller by the high shear agitation, the quantity of solid particle stabilizer, such as hydrophobically surfaced silica, required of a given size increases in order to cover the entire surface of the oil-phase droplets and prevent the uncontrolled coalescence of the liquid droplets, thereby achieving uniform size and size distribution of the liquid droplets that result.

The O/O compositions according to the present invention can be used in a variety of applications, either known or newly developed applications, including electro-optical modulating display devices, meaning display devices in which the optical state of an imaging material is modulated or changed by subjecting the imaging material to at least an electric field or the transport of electrons, for example, electrophoretic, electrowetting, and electrochromic display devices. Imaging applications include, for example, migration imaging and liquid toning systems, which use electrostatics for ink fractionation and transfer. Industrial applications include, for example, coatings and lubricating films for mechanical devices.

In one particular embodiment of the invention, the O/O composition is useful as the display fluid of electro-optical modulated display devices such as electrophoretic displays which comprises colored particles dispersed in a liquid system. The liquid system preferably contains from about 50 to about 95% by weight of the continuous phase and about 5 to about 50% by weight of the colored dispersed oil droplets.

The invention will further be illustrated by the following examples:

EXAMPLES

TUFTONE NE-303, a bisphenol A polyester resin polymer (density 1.16 g/cc), used in the examples below was obtained from Kao Specialties Americas LLC a part of Kao Corporation, Japan. The carbon black pigment REGAL 330 (density 1.8 g/cc) used in the examples was obtained from Cabot Corporation, Billerica, Mass. SUNFAST blue 15:3 (PB 15:3) and SUNFAST magenta 122 (PR122) the colored pigments used were obtained from Sun Chemicals. Triethyl phosphate (TEP) and n-dodecane were purchased from Aldrich Chemical Co., Milwaukee, Wis. The co-stabilizer OLOA 11,000, a polyisobutylene succinimide, 62% active in mineral oil, was obtained from Chevron in San Ramon, Calif. SANDUVOR 3058 (N-(1-Acetyl-2,2,6,6-tetramethyl-4-piperidinyl)-2-dodecylsuccinimide) was obtained from Clariant. The hydrophobially surfaced silicas used in the examples, hydrophobic silane treated fumed silica, CAB-O-SIL Nanogel Grade 08N Translucent Aerogel (CS-1) and TS 610 (CS-2) were purchased from Cabot Corporation, Tuscola, Ill.

Table 1 below lists various oil phase compositions and their properties. Viscosities were measured using a Brookfield cone/plate viscometer at 25° C. The other parameters were obtained from various published literature sources and the densities of the oil phases containing additives were calculated from weighted averages.

TABLE 1

| Oil Composition | Viscosity (mPa, 25° C.) | Density (g/cc) | Refractive Index | Dielectric Constant (20° C.) | Boiling Point ° C. (atm P) |
|---|---|---|---|---|---|
| TEP | 1.8 | 1.072 | 1.405 | 13.2 | 215 |
| TEP + TUFTONE NE-303 (80/20w/w) | 37.3 | 1.09 | | | |
| TEP + TUFTONE NE-303 + REGAL 330 (80/15/5w/w/w) | 29.4 | 1.12 | | | |
| Dodecane | 1.38 | 0.75 | 1.421 | 2.01 | 215 |

Examples 1-3

A pigment-polymer resin composite (4 g) comprising 25 weight % pigment (either carbon black or the colored pigments) and 75 weight % TUFTONE NE-303 polymer was dissolved in 16 g of TEP. This was dispersed in 50 g of dodecane containing 0.125 g of OLOA 11,000 (100% active) and 1.75 g of CS-1 using an overhead SILVERSON L4R mixer from Silverson for one minute at maximum speed. The resultant dispersion was further homogenized using a MICROFLUIDIZER Model #110T from Microfluidics at a pressure of 12,000 lbs/sq inch until a fine dispersion was obtained. The number median D(n) and volume median D(v), particle sizes were measured using low angle laser light scattering with a MALVERN ZETASIZER ZS that uses a 633 nm wavelength, 4 mW He—Ne laser. The median (50%) is the value of the particle size which divides the population exactly into two equal halves such that there is 50% distribution above this value and 50% below. The emulsion described in these examples and the following examples were stable for several months at ambient temperature as shown by minimum settling and unchanged particle size.

Examples 4-6

These examples were made using the same method as described in Examples 1-3 except that 3 g of TUFTONE NE-303 polymer was used as the resin without any pigment in Example 4, a different silica was used in Example 5, and no OLOA 11000 dispersant was used in Example 6.

The particles sizes obtained for Examples 1-6 are shown in Table 2 below. Without the OLOA co-stabilizer, no stable particles formed in Example 6. All the other examples produced particles that have very narrow particle size distributions as evidenced by the tight CV for the number median particle size. Further the D(n) and D(v) values are very similar in each example once again demonstrating a uniform particle size distribution. CS-2 silica gave a somewhat bigger size compared to CS-1 showing the effect of different silicas on the resulting particle size of the O/O emulsion.

TABLE 2

| Example | Pigment | Silica Type | Particle Size D(n)(50%) Microns | CV number | Particle Size D(v)(50%) microns |
|---|---|---|---|---|---|
| 1 | REGAL 330 | CS-1 | 1.76 | 21 | 1.9 |
| 2 | Pigment Red 122 | CS-1 | 1.39 | 18 | 1.6 |
| 3 | Pigment Blue 15:3 | CS-1 | 1.40 | 17 | 1.5 |
| 4 | None | CS-1 | 1.24 | 17 | 1.3 |
| 5 | REGAL 330 | CS-2 | 2.52 | 20 | 2.7 |
| 6 | REGAL 330 | CS-1 | None | | |

Examples 7-9

In these examples, the procedure followed was the same as in Example, except that SANDUVOR 3058 was used as the co-stabilizer in place of OLOA 11000. Further, the amounts of SANDUVOR 3058 and the fumed silica levels were varied as shown in Table 3 below. When the level of SANDUVOR co-stabilizer was increased for the same amount of silica, in Examples 7 and 8, the overall particle size decreased. Similarly, as the level of silica increased, in Examples 7 and 9, the size again decreased. In all cases, the size distribution was relatively narrow.

TABLE 3

| Example | Weight of SANDUVOR 3058 | Weight of CS-1 | Particle Size D(n)(50%) microns | CV number | Particle Size D(v)(50%) microns |
|---|---|---|---|---|---|
| 7 | 0.125 | 1.75 | 4.08 | 19 | 4.34 |
| 8 | 0.25 | 1.75 | 1.16 | 19 | 1.22 |
| 9 | 0.125 | 3.5 | 1.12 | 19 | 1.18 |

The invention has been described with reference to a preferred embodiment. However, it will be appreciated that variations and modifications can be effected by a person of ordinary skill in the art without departing from the scope of the invention.

The invention claimed is:

1. An oil-in-oil emulsion comprising a first oil phase dispersed as liquid droplets in a continuous second oil phase, which liquid droplets have a number median diameter of about 1 μm to 10 μm,
  wherein the first oil phase comprises one or more first oils and colorant, the colorant being selected from the group consisting of a pigment, polymer, laked pigment, dye, pigment-polymer composite, dye-polymer composite, and a combination of these materials, and the second oil phase comprises one or more second oils,
  wherein the liquid droplets are substantially covered with a layer of hydrophobically surfaced solid particles, wherein the concentration of hydrophobically surfaced solid particles is from 5 to about 75 weight percent with respect to the first oil phase,
  wherein the one or more first oils comprises a liquid organic phosphate compound, the liquid organic phosphate compound being selected from the group consisting of branched or unbranched alkyl, cycloalkyl, alkylcycloalkyl, aryl, and alkaryl phosphates, in which the organic groups may be substituted or unsubstituted,
  wherein the second oil phase comprises one or more solvents selected from the group consisting of substantially non-polar substituted or unsubstituted C6-C20 alkanes, substituted or unsubstituted aromatic hydrocarbons, and mixtures thereof,
  wherein the dielectric constant at 20° C. of the first oil phase and the second oil phase, respectively, are both independently less than 25, before the addition of any solid additives to the phases,
  wherein the hydrophobically surfaced solid particles have an average particle size of from about 1 nm to 100 nm, and comprise inorganic particles surface treated with a hydrophobic material, and
  wherein the oil-in-oil emulsion further comprises a co-stabilizer that is soluble in the continuous second oil phase, for enhancing the adsorption of the hydrophobically surfaced solid particles at the interface of the first oil phase droplets and the continuous second oil phase.

2. The composition of claim 1 wherein the hydrophobically surfaced solid particles comprise silica particles that have been treated to form a hydrophobic surface on the particles.

3. The composition of claim 1 wherein the co-stabilizer comprises one or more compounds selected from the group consisting of polyethyleneimine substituted succinimide derivative of polyisobutylene; N-(1-acetyl-2,2,6,6-tetramethyl-4-piperidinyl)-2-dodecylsuccinimide; 2-dodecyl-N-(2,2,6,6-tetramethyl-4-piperidinyl)-succinimide; and 2-dodecyl-N-(1,2,2,6,6-pentamethyl-4-piperidinyl)-succinimide.

4. The composition of claim 1 wherein the refractive index of the one or more first oils in the continuous second oil phase is substantially matched to that of the one or more first oils in the dispersed first oil phase such that the difference between the respective refractive indices is between about zero and about 0.3.

5. The composition of claim 4 wherein the difference between the respective refractive indices is between about 0.05 and about 0.2.

6. The composition of claim 1 wherein the continuous second oil phase has a dielectric constant less than 10.

7. The composition of claim 1 wherein the organic phosphate compound has a boiling point greater than about 100° C. at atmospheric pressure, a dielectric constant less than 25, and a viscosity less than 100 cP at 25° C.

8. The composition of claim 1 where the first oil phase, including the one or more first oils and optional polymers, colorants, or other additives in the dispersed phase liquids, has a viscosity less than 200 cP at 25° C.

9. The composition of claim 1 wherein the first oil phase comprises one or more oils selected from the group consisting of trialkylphosphates and triarylphosphates.

10. The composition of claim 1 wherein the boiling point of the one or more first oils in the dispersed first oil phase and the continuous second oil phase is independently greater than 100° C. at atmospheric pressure.

11. The composition of claim 1 wherein the dispersed first oil phase is present in the amount of 1 to 50 weight percent of the continuous second oil phase.

12. The emulsion composition of claim 1 further comprising a polymer.

13. The composition of claim 12 wherein the dispersed first oil phase comprises a molecularly dissolved polymer.

14. The composition of claim 13 wherein the molecularly dissolved polymer is a polyester.

15. The composition of claim 1 wherein the dispersed first oil phase further comprises both a colorant and a molecularly dissolved polymer.

16. The composition of claim 12 wherein the dispersed first oil phase comprises colorant in an amount 1 to 30 percent by weight of the dispersed first oil phase.

17. The composition of claim 1 wherein a pigment, polymer, and/or pigment-polymer composite is present in the dispersed first oil phase in a total amount of from 1 to about 50 percent by weight of the dispersed phase and wherein the one or more first oils is present in the amount of from 50 to 99 percent by weight of the dispersed phase.

* * * * *